United States Patent [19]

Hrib

[11] Patent Number: 5,034,392
[45] Date of Patent: Jul. 23, 1991

[54] 4-(3-(4-OXOTHIAZOLIDINYL)BUTYNYLA-MINES

[75] Inventor: Nicholas J. Hrib, Somerville, N.J.

[73] Assignee: Hoechst-Roussel Pharmaceuticals Incorporated, Somerville, N.J.

[21] Appl. No.: 509,280

[22] Filed: Apr. 16, 1990

[51] Int. Cl.$^5$ ................ A61K 31/495; A61K 31/445; C07D 417/06; C07D 417/14
[52] U.S. Cl. .................................... 514/252; 514/278; 514/321; 514/322; 514/326; 514/230; 514/360; 514/364; 514/369; 546/15; 546/20; 546/198; 546/199; 546/201; 546/209; 546/216; 546/217; 546/225
[58] Field of Search ...................... 544/364, 369, 230; 546/15, 20, 199, 201, 216, 217, 225; 514/252, 278, 321, 322

[56] References Cited

U.S. PATENT DOCUMENTS 3,354,178 11/1967 Dickinson ........................... 544/372
4,933,453 6/1990 Hrib et al. .......................... 544/297

OTHER PUBLICATIONS

P. Moses et al., Acetylene Compounds of Potential Pharmacological Value, Acta. Pharm. Succ., 15, 1978, pp. 175–180.

Primary Examiner—Cecilia Shen
Attorney, Agent, or Firm—Elliott Korsen

[57] ABSTRACT

This invention relates to compounds of the formula

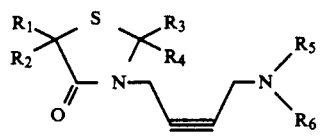

where $R_1$ and $R_2$ are independently hydrogen or loweralkyl or $R_1$ and $R_2$ taken together with the carbon atom to which they are attached form a spiro-fused cycloalkane of 5 to 8 carbons; $R_3$ and $R_4$ are independently hydrogen or loweralkyl or $R_3$ and $R_4$ taken together with the carbon atom to which they are attached form a spiro-fused cycloalkane of 5 to 8 carbons; $R_5$ and $R_6$ taken together with the nitrogen atom to which they are attached are

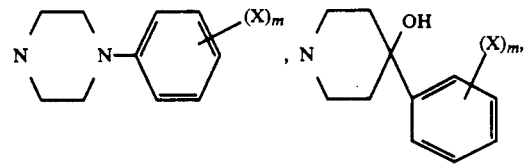

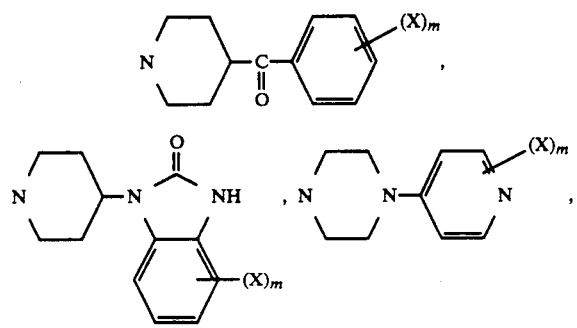

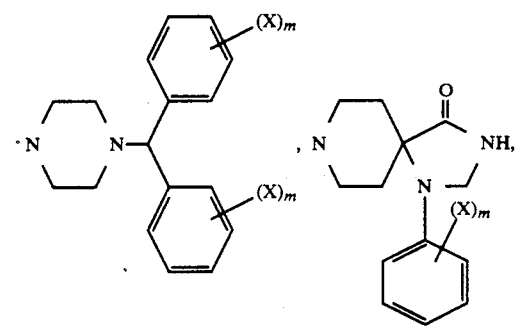

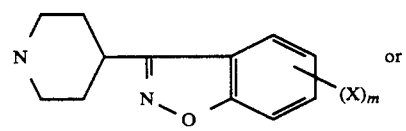

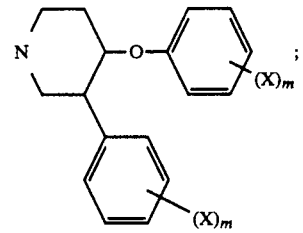

where X in each occurrence is independently hydrogen, halogen, loweralkyl, hydroxy, nitro, amino, cyano, trifluoromethyl or methoxy; and m is 0, 1 or 2; the pharmaceutically acceptable acid addition salts thereof and where applicable the optical and geometrical isomers and racemic mixtures thereof. The compounds of this invention are useful as analgesic and antihypertensive agents.

22 Claims, No Drawings

4-(3-(4-OXOTHIAZOLIDINYL)BUTYNYLAMINES

This invention relates to compounds of the formula

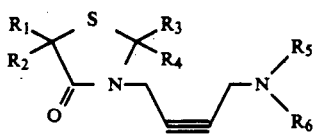

where $R_1$ and $R_2$ are independently hydrogen or loweralkyl or $R_1$ and $R_2$ taken together with the carbon atom to which they are attached form a spiro-fused cycloalkane of 5 to 8 carbons; $R_3$ and $R_4$ are independently hydrogen or loweralkyl or $R_3$ and $R_4$ taken together with the carbon atom to which they are attached form a spiro-fused cycloalkane of 5 to 8 carbons; $R_5$ and $R_6$ taken together with the nitrogen atom to which they are attached are

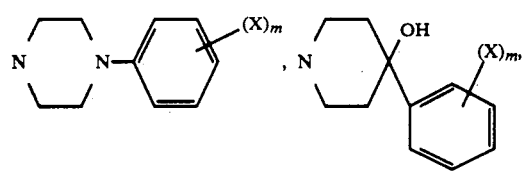

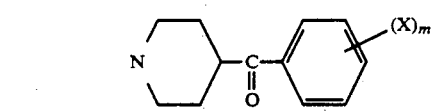

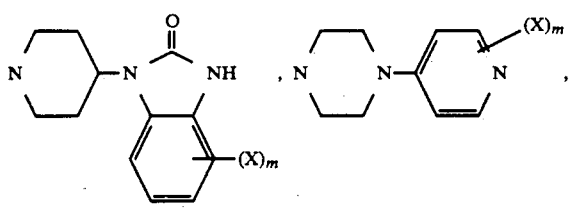

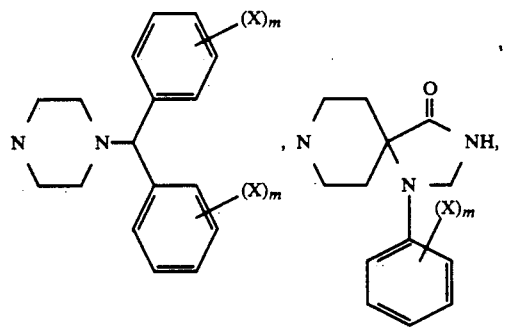

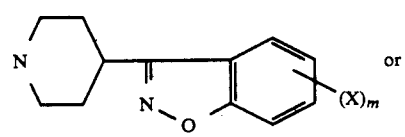 or

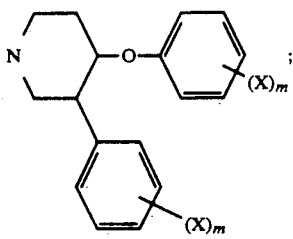

where X in each occurrence is independently hydrogen, halogen, loweralkyl, hydroxy, nitro, amino, cyano trifluoromethyl or methoxy; and m is 0, 1 or 2; the pharmaceutically acceptable acid addition salts thereof and where applicable the optical and geometrical isomers and racemic mixtures thereof. The compounds of this invention are useful as analgesic and antihypertensive agents.

Throughout the specification and appended claims, a given chemical formula or name shall encompass all geometric and optical isomers and racemic mixtures where such isomers and mixtures exist. Additionally, a given chemical formula or name shall encompass pharmaceutically acceptable acid addition salts thereof and solvates thereof such as for instance hydrates.

In the above definitions, the term "lower" means the group it is describing contains from 1 to 6 carbon atoms. The term "alkyl" refers to a straight or branched chain hydrocarbon containing no unsaturation, e.g., methyl, ethyl, propyl, isopropyl, 2-butyl, neopentyl, n-hexyl, etc.; the term "aryl" refers to a monovalent substituent which consists of a group, e.g., phenyl, o-tolyl, m-methoxyphenyl, etc., of the formula

where Z is hydrogen, halogen, loweralkyl, loweralkoxy, trifluoromethyl, nitro and amino and p is an integer of 1 to 4; the term "cycloalkane" refers to a substituent consisting of a saturated hydrocarbon possessing at least one carbocyclic ring of 3 to 8 carbon atoms, e.g., cyclopropane, cyclobutane, cyclopentane, cyclohexane, etc. Said cycloalkane may be substituted with 1 or 2 loweralkyl groups, and it may also be sutstituted at one of the ring carbons so as to form a spiro compound each constituent ring of which being a cycloalkyl of 3 to 8 carbon atoms. The term alkoxy refers to a monovalent substituent which consists of an alkyl group linked through an ether oxygen having its free valence bond from the ether oxygen, e.g., methoxy, ethoxy, propoxy, butoxy, pentoxy, etc.; and the term halogen refers to a member of the halogen family consisting of fluorine, chlorine, bromine and iodine.

The compounds of the present invention are prepared in the following manner. The substituents, $R_1$, $R_2$, $R_3$, $R_4$, $R_5$, $R_6$, X and m are as defined above unless indicated otherwise.

Compound II of the formula

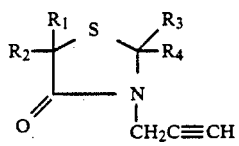 (II)

is reacted with formaldehyde or a formaldehyde equivalent and an amine selected from the group consisting of

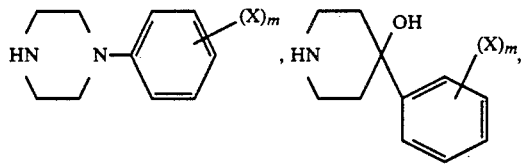

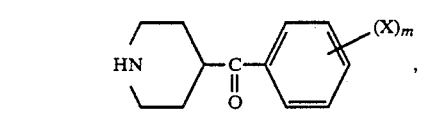

in an addition type reaction to afford Compound I of the invention where $R_1$, $R_2$, $R_3$ and $R_4$ are hydrogen. This reaction is typically conducted in a solution containing an ethereal solvent such as dioxane with paraformaldehyde to which a catalyst such as cuprous chloride is added. This reaction takes place at a temperature of about 25° to 90° C. for 1 to 24 hours. This reaction may optionally be conducted in an inert atmosphere, i.e., under nitrogen gas.

Compound III of the formula

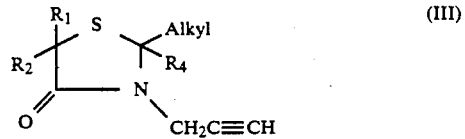 (III)

where alkyl is as previously defined, is reacted with formaldehyde or a formaldehyde equivalent and an amine selected from the group listed above in an addition type reaction to afford Compound I of the invention where $R_3$ is alkyl.

This reaction also typically takes place in the presence of an ethereal solvent such as dioxane, tetrahydrofuran etc., with paraformaldehyde and a catalyst such as cuprous chloride at a temperature of 25° to 90° C. for 1 to 24 hours.

Compound IV of the formula

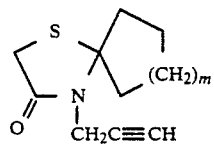 (IV)

where m is 1, 2 or 3, is similarly reacted with one of the amines listed earlier to afford Compound I of the invention where $R_3$ and $R_4$ taken together with the carbon atom to which they are attached form a spiro-fused cycloalkane of 5 to 8 carbons.

The compounds of the present invention are useful as analgesic agents due to their ability to alleviate pain in mammals. The activity of the compounds is demonstrated in the phenyl-para-quinone writhing assay in mice, a standard assay for analgesia [*Proc. Soc. Exptl. Biol. Med.*, 95, 729 (1957)]. The analgesic activity of some of the compounds of the invention expressed in terms of percent inhibition of writhing is given in Table 1.

TABLE 1

| Compound | % Inhibition of Writhing at 20 mg/kg s.c. |
| --- | --- |
| 2-Methyl-3-(4-(4-hydroxy-4-phenylpiperidino)-2-butynyl)-4-oxothiazolidine oxalate | 51% |
| 3-(4-[3-(4-piperidyl)-6-chlorobenzisoxazole]-2-butynyl)-4-oxothiazolidine oxalate | 39% |
| 3-(4-(1-(4-chlorobenzhydryl)-piperazino)-2-butynyl)-1-thia-4-azaspiro[4.4]nonane-4-one tris-oxalate | 30% |
| ibuprofen (standard) | 50 at 10.4 mg/kg s.c. |
| pentazocine (standard) | 50% at 1.3 mg/kg s.c. |

The analgesic relief of pain is achieved when the compounds of the inventions are administered to a subject requiring such treatment at an effective oral, parenteral or intravenous dose of from 0.01 to 100 mg/kg of body weight per day. A preferred effective dose within this range is from about 10 to 50 mg/kg of body weight per day. A particularly preferred effective amount is about 30 mg/kg of body weight per day. It is to be understood, however, that for any particular subject, specific dosage regimens should be adjusted according to the individual need and the professional judgment of the person administering or supervising the administration of the compound. It is further to be understood that the dosages set forth herein are exemplary only and that they do not, to any extent, limit the scope or practice of the invention.

The compounds of the present invention are also useful as antihypertensive agents due to their ability of lower blood pressure in mammals. Antihypertensive activity is measured in the spontaneous hypertensive rat by the indirect tail cuff method. The indirect tail cuff method is described in "Methods in Pharmacology", A. Schwartz. ed., Vol. I, Appleton-Century Crofts, New York, N.Y., 1971, p. 135. In this procedure a group of five animals is treated orally for three days with the test compound in relation to a control group of the same number. The drop in blood pressure is measured on the third day following administration. The antihypertensive activity of representative compounds of the invention, expressed as decrease in mean arterial blood pressure (in mm Hg) is given in Table 2.

TABLE 2

| Compound | mm Hg decrease at 50 mg/kg p.o |
|---|---|
| 3-[4-(1-(2-methoxyphenyl)piperazino)-2-butynyl]-4-oxothiazolidine sesquioxalate | 51 |
| 3-[4-(1-(4-fluorophenyl)piperazino)-2-butynyl]-4-oxothiazolidine oxalate | 71 |
| 3-(4-(4-pyridyl)piperazino)-2-butynyl)-4-oxothiazolidine sesquioxalate | 30 |
| 3-(4-(1-(4-chlorobenzhydryl)piperazino)-2-butynyl)-4-oxothiazolidine bis maleate | 28 |
| standard guanethidine | 20 |

Blood pressure reduction is achieved when the compounds of the invention are administered to a subject requiring such treatment at an effective oral, parenteral or intravenous dose of from 0.1 to 50 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are exemplary only and that they do not, to any extent, limit the scope or practice of the invention.

Effective amounts of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier or they may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such compositions is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose; a disintegrating agent such as alginic acid, Primogel TM, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the doseage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:
3-[4-(1-(2-Methoxyphenyl)piperazino-2-butynyl]-4-oxothiazolidine sesquioxalate;
2-Methyl-3-(4-(4-hydroxy-4-phenylpiperidino)-2-butynyl)-4-oxothiazolidine oxalate;
3-(4-4-(4-Fluorobenzoyl)piperidino)-2-butynyl)-4-oxothiazolidine oxalate;
3-[4-(4-(1,3-Dihydro-2-oxo-2H-benzimidazol-1-yl)piperidino)-2-butynyl]-4-oxothiazolidine hemioxalate hemihydrate;

3-(4-(1-(4-Fluorophenyl)piperazino)-2-butynyl-4-oxo-
thiazolidine oxalate;
3-(4-(4-Pyridinyl)piperazino)-2-butynyl)-4-oxothiazoli-
dine sesquioxalate;
3-(4-(1-(4-Chlorobenzhydryl)piperazino)-2-butynyl)-4-
oxothiazolidine bis maleate;
3-(4-(1-Phenyl-1,3,8-triazaspiro[4.5]-decan-4-one)-2-
butynyl)-4-oxothiazolidine oxalate;
4-(4-(1-(2-Methoxyphenyl)piperazino)-2-butynyl)-1-
thia-4-azaspiro[4.4]nonane-3-one hydrochloride hydrate;
3-(4-[3-(4-Piperidyl)-6-chloro-benzisoxazole]-2-
butynyl)-4-oxothiazolidine oxalate;
3-(4-1-(4-(4-Bromophenoxy)-3-phenyl-piperidyl)-2-
butynyl)-4-oxothiazolidine oxalate hydrate;
4-(4-(1-(4-Chlorobenzhydryl)piperazino)-2-butynyl)-1-
thia-4-azaspiro[4.4]nonane-3-one trisoxalate;
2-Methyl-3-(4-(4-(4-bromo)phenoxy)-3-phenyl-
piperidyl)-2-butynyl)-4-oxothiazolidine oxalate hemihydrate;
2-Methyl-3-(4-1-(2-methoxyphenyl)piperazino-2-
butynyl)-4-oxothiazolidine;
3-[4-(1-(2-Methoxyphenyl)piperazino-2-butynyl)-1-thia-
3-azaspiro[4.4]nonan-4-one;
4-(4-(4-Hydroxy-4-phenylpiperidino)-2-butynyl)-1-thia-
4-azaspiro[4.5]decan-3-one;
5,5-Dimethyl-3(4-(1-(4-fluorophenyl)piperazino)-2-
butynyl-4-oxothiazolidine;
5-Ethyl-3-(4-(4-pyridinyl)piperazino)-2-butynyl-4-oxo-
thiazolidine;
2-Methyl-3-[4-(4-(4-fluorobenzoyl)piperidino]-2-
butynyl]-1-thia-3-azaspiro[4.4]nonan-4-one;
2,2,5,5-Tetramethyl-3-[4-(4-(1,3-dihydro-2-oxo-2H-ben-
zimidazol-1-yl)piperidino-2-butynyl]-4-oxothiazolidine;
2-Methyl-3-[4-(4-(2-pyridinyl)piperazino)-2-butynyl]-1-
thia-3-azaspiro[4.4]nonane-4-one.

The following examples are for illustrative purposes
only and are not to be construed as limiting the invention. All temperatures are given in degrees centrigrade
unless indicated otherwise.

EXAMPLE 1

3-Propargyl-4-oxothiazolidine

To a stirred solution of 10.3 g of 4-oxothiazolidine in
500 ml of anhydrous dimethylformamide under N₂ was
added 6.0 g of sodium hydride (50% in oil). After 30
min., 15 ml of a solution of 80% propargyl bromide in
toluene was added and the mixture was allowed to stir
for another hour. The mixture was then poured into
saturated aqueous sodium bicarbonate and extracted
with ethyl acetate. The combined organic fractions
were washed twice with water, then once with brine,
dried (MgSO₄), filtered and concentrated. The residue
was distilled at 0.1/mm Hg, 95°–98° C., to provide 9.248
g of 3-propargyl-4-oxothiazolidine as an oil which solidified upon refrigeration, mp 29°–31°.

Analysis: Calculated for C₆H₇NOS: 51.04%C
4.99%H 9.92%N Found: 50.99%C 5.15%H 9.80%N.

EXAMPLE 2

2-Methyl-3-propargyl-4-oxothiazolidine

To 10.0 g 2-methyl-4-oxothiazolidine in 450 ml anhydrous dimethylformamide was added 5.13 g of sodium
hydride (50% dispersion in oil). The mixture was placed
under N₂ gas and allowed to stir at room temperature
for 30 minutes, after which 12.8 ml of propargyl bromide (90% in toluene) was added. The reaction mixture
was allowed to stir at room temperature for 3.5 hours.
No starting material remained as shown by TLC (silica,
100% ethyl acetate).

The reaction mixture was poured into an equivalent
volume of saturated aqueous sodium bicarbonate solution and extracted four times with 150 ml portions of
ethyl acetate. The combined organic layers were
washed twice with water and once with saturated NaCl
solution. The organic layer was dried (MgSO₄), filtered,
and concentrated in vacuo to yield 21.2 g of a crude oil.
The oil was chromatographed on silica using 3:1 hexane:ethyl acetate eluent to give 4.7 g of 2-methyl-3-propargyl-4-oxothiazolidine as an oil.

Analysis: Calculated for C₇H₉NOS: 54.17% C,
5.84% H, 9.02% N; Found: 54.08% C, 5.97% H, 8.71%
N.

Example 3

3-[4-(1-(2-Methoxyphenyl)piperazino)-2-butynyl]-4-
oxothiazolidine sesquioxalate To a solution of 3-propargyl-4-oxothiazolidine (4.00
g), paraformaldehyde (1.02 g) and 1-(2-methoxyphenyl)piperazine (6.54 g) in approximately 20 ml sieve-dried dioxane was added 0.84 g coprous chloride. The
reaction mixture was left stirring at room temperature
for approximately 15 hours and then was equipped with
a reflux condenser and heated to 80° C. After about 8.5
hours with heat, no starting material remained in the
reaction as observed by thin layer chromatography
(TLC hereafter) (silica, 100% ethyl acetate). The reaction mixture was allowed to cool to room temperature
and then it was filtered and diluted with dioxane and
100 ml H₂O. The mixture was transferred to a separatory funnel, acidified with 3N HCl, and washed twice
with 100 ml portions of ether. The aqueous fraction was
basified by the addition of Na₂CO₃ and extracted with
dichloromethane. The dichloromethane fractions were
dried (MgSO₄), filtered, and concentrated in vacuo.
The residue was dissolved in dichloromethane, a precipitate was filtered off, and the filtrate was concentrated in vacuo. The oxalate salt was precipitated from
ethyl acetate and recrystallized form ethyl acetate/ethanol and methanol/toluene to yield 1.06 g of 3-[4-(1-
(2-methoxyphenyl)piperazino)-2-butynyl]-4-oxo-
thiazolidine sesquioxalate, m.p. 159°–161° C.

Analysis: Calculated for C₂₁H₂₆N₃O₈S: 52.49% C,
5.45% H, 8.47% N; Found: 52.51% C, 5.37% H, 8.67%
N.

Example 4

2-Methyl-3-(4-(4-hydroxy-4-phenylpiperidino)-2-
butynyl)-4-oxothiazolidine oxalate To a solution of 2-methyl-3-propargyl-4-oxothiazolidine (3.52 g), paraformaldehyde (0.82 g) and 4-hydroxy-
4-phenylpiperidine (4.83 g) in approximately 12 ml
sieve-dried dioxane was added 0.67 g of cuprous chloride. The reaction flask was equipped with a reflux
condenser and heated to 60° C. After 1 hour no starting
material remained in the reaction mixture as observed
by TLC (1:1, hexane:ethyl acetate). The reaction mixture was cooled, filtered, diluted with 100 ml H₂O,
acidified with 3N HCl and washed twice with 100 ml
portions of ether.

The aqueous fraction was basified by addition of
Na₂CO₃ and extracted with dichloromethane. The dichloromethane fractions were dried (MgSO₄), filtered, and concentrated in vacuo to yield 10.24 g of an oil. The crude oil was passed through an alumina column using 2:1, hexane:ethyl acetate as an eluent to yield 5.44 g of material. A second column of silica was run using 1:1, hexane:ethyl acetate followed by 1:2, hexane:ethyl acetate as an eluent to yield 1.92 g of material. This material hygroscoped into a gum. The gum was passed through a flash column of silica using ethyl acetate as an eluent. The oxalate salt of the resulting residue was precipitated from ether. The yield was 0.858 g of 2-methyl-3-(4-(4-hydroxy-4-phenylpiperidino)-2-butynyl)-4-oxothiazolidine oxalate, m.p. 135.5°–138.5° C.

Analysis: Calculated for $C_{21}H_{26}N_2O_6S$: 58.05% C, 6.03% H, 6.45% N; Found: 57.69% C, 6.20% H, 6.33% N.

Example 5

3-(4-4-(4-Fluorobenzoyl)piperidino)-2-butynyl)-4-oxothiazolidine oxalate

To a solution of 3-propargyl-4-oxothiazolidine (5.02 g), paraformaldehyde (1.28 g) and 4-(4-fluorobenzoyl)-piperidine hydrochloride (10.36 g) in triethylamine (7.20 g) and approximately 20 ml sieve-dried dioxane was added 1.06 of cuprous opper chloride. The reaction flask was equipped with a reflux condenser and heated to 80° C. After 3 hours no starting material remained as observed by TLC (1:1, hexane:ethyl acetate). The reaction mixture was cooled to room temperature, diluted with dichloromethane, filtered, and concentrated in vacuo. The residue was taken up in dichloromethane and extracted with acidic aqueous medium. The combined aqueous fractions were basified by addition of $Na_2CO_3$ and extracted with dichloromethane. Combined dichloromethane fractions were dried ($MgSO_4$), filtered, and concentrated in vacuo. The residue was dissolved in ethyl acetate and filtered. The oxalate salt was precipitated from ethyl acetate and recrystallized from methanol/ethyl acetate and methanol/toluene to yield 2.34 g of 3-(4-4-(4-fluorobenzoyl)piperidino)-2-butynyl)-4-oxothiazolidine oxalate, m.p. 128.5°–129.5° C.

Analysis: Calculated for $C_{19}H_{21}FN_2O_2S \cdot C_2H_2O_4$: 55.99% C, 5.15% H, 6.22% N; Found: 55.68% C, 5.29% H, 6.09% N.

Example 6

3-[4-(4-(1,3-Dihydro-2-oxo-2H-benzimidazol-1-yl)-piperidino)-2-butynyl]-4-oxothiazolidine hemioxalate hemihydrate To a solution of 3-propargyl-4-oxothiazoidine (5.07 g), paraformaldehyde (1.29 g) and 4-[1,3-dihydro-2-oxo-2H-benzimidazol-1-yl]piperidine (9.37 g) in 35 ml sieve-dried dioxane was added 1.07 g of cuprous chloride. The reaction flask was equipped with a reflux condenser and heated to 68° C. After 24 hours no starting material remained in the reaction mixture as observed by TLC (silica, 2:1, hexane:ethyl acetate). The reaction mixture was filtered through filter paper and diluted with dichloromethane. The resulting organic mixture was extracted five times with 150 ml portions of 3N HCl solution.

The aqueous fractions were combined and basified by addition of potassium carbonate and extracted with dichloromethane. The combined dichloromethane fractions were dried ($MgSO_4$), filtered, and concentrated in vacuo. The oxalate salt was precipitated from ethyl acetate and recrystallized from methanol/ethyl acetate to yield 0.83 g of 3-[4-(4-(1,3-dihydro-2-oxo-2H-benzimidazol-1-yl)piperidino)-2-butynyl]-4-oxothiazolidine hemioxalate hemihydrate, m.p. 202°–204° C.

Analysis: Calculated for $C_{19}H_{22}N_4O_2S \cdot \frac{1}{2}H_2O \cdot \frac{1}{2}C_2H_2O_2$: 56.59% C, 5.70% H, 13.20% N; Found: 56.66% C, 5.61% H, 13.30% N.

Example 7

3-(4-(1-(4-Fluorophenyl)piperazino)-2-butynyl-4-oxothiazolidine oxalate

To a solution of 3-propargyl-4-oxothiazolidine (5.15 g), paraformaldehyde (1.31 g), and 1-(4-fluorophenyl)-piperazine (7.89 g) in approximately 20 ml sieve-dried dioxane was added 1.08 g of cuprous chloride. The reaction flask was heated in an oil bath to 87° C. with a reflux condenser attached to it. After 24 hours, no starting material remained in the reaction mixture as observed by TLC (silica, 2:1, hexane:ethyl acetate). The reaction mixture was allowed to cool to room temperature, filtered through filter paper, diluted with dichloromethane, and extracted four times with 125 ml portions of 3N HCl solution.

The aqueous fraction was basified by addition of $Na_2CO_3$ and extracted with dichloromethane. The dichloromethane fractions were dried ($MgSO_4$), filtered, and concentrated in vacuo to yield 8.76 grams crude product. The crude residue was passed through a silica column with ethyl acetate as the eluent. The oxalate salt was precipitated from ethyl acetate and recrystallized from methanol/toluene to yield 1.38 g of 3-(4-(1-(4-fluorophenyl)piperazino)-2-butynyl-4-oxothhiazolidine oxalate, m.p. 160.5°–162° C.

Analysis: Calculated for $C_{17}H_{20}FN_3OS \cdot C_2H_2O_4$: 53.89% C, 5.24% H, 9.92N %; Found: 53.93% C, 5.21% H, 9.93% N.

Example 8

3-(4-(4-Pyridyl)piperazino)-2-butynyl)-4-oxothiazolidine sesquioxalate

A mixture of 3-propargyl-4-oxothiazolidine (5.0 g), paraformaldehyde (1.4 g), 1-(4-pyridyl)piperazine (5.8 g) and 1.0 g of cuprous chloride in 20 ml anhydrous dioxane, was heated to 80° with stirring under $N_2$. After 18 hr. the mixture was cooled to room temperature, diluted with dichloromethane, and filtered. The filtrate was concentrated in vacuo, and then filtered through a pad of silica using methanol as eluent. This filtrate was concentrated in vacuo, taken up in ethyl acetate, filtered to remove residual silica, and treated with a solution of oxalic acid in ethyl acetate. The precipitated oxalate salt was collected and dried in vacuo to provide 3.782 g of the sesquioxalate as a powder, m.p. 163°–166° C. (dec.).

Analysis: Calculated for $C_{16}H_{20}N_4OS \cdot 1.5C_2H_2O_4$: 50.54% C, 5.14% H, 12.40% N; Found: 50.45% C, 5.35% H, 12.00% N.

Example 9

3-(4-(1-(4-Chlorobenzhydryl)piperazino)-2-butynyl)-4-oxothiazolidine bis maleate To a solution of 3-propargyl-4-oxothiazolidine (5.15 g) 1-(4-Chlorobenzhydryl)-piperazine (7.30 g), and paraformaldehyde (1.32 g) in approximately 30 ml sieve-dried dioxane was added 1.09 g of curpous chloride. The reaction flask was equipped with a reflux condenser, placed under nitrogen gas, and heated in an oil bath to 73° C. After 1 hour there was no starting amine in the reaction mixture as observed by TLC (silica, 100% methanol, 10/90, methanol/ethyl acetate. The reaction mixture was cooled to room temperature, filtered, and concentrated in vacuo. The residue was taken up in ethyl acetate, filtered again, and concentrated in vacuo again. The resulting oil was passed through silica gel with ethyl acetate as an eluent. The maleate salt was precipitated from ether yielding 3.46 g of 3-(4-(1-(4-chlorobenzhydryl)piperazino)-2-butynyl)-4-oxothiazolidine bis maleate, m.p. 135°–138° C.

Analysis: Calculated for $C_{26}H_{28}ClN_3OS \cdot 2CH_2O_4$: 57.18% C, 5.10% H, 5.27% N. Found: 57.14% C, 5.01% H, 5.12% N.

Example 10

3-(4-(1-Phenyl-1,3,8-triazaspiro[4.5]-decan-b 4-one)-2-butynyl)-4-oxothiazolidine oxalate To a solution of 3-propargyl-4-oxothiazolidine (4.57 g), paraformaldehyde (1.17 g) and 1-phenyl-1,3,8-triazaspiro[4.5]-decan-4-one (5.0 g) in 25 ml sieve-dried dioxane was added 0.96 g of cuprous chloride. The reaction mixture was heated under $N_2$ gas to 77° C.

After approximately 18 hours the reaction mixture contained no starting amine as observed by TLC (silica, 100% methanol). The reaction mixture was cooled to room temperature, filtered, and concentrated in vacuo. The residue was taken up in ethyl acetate, filtered, and concentrated in vacuo to yield 9.7 grams of an oil. The oil was chromatographed on silica with eluent of ethyl acetate and the fractions containing the desired product were concentrated in vacuo. The oxalate salt was precipitated from ethyl acetate and recrystallized from acetonitrile to yield 2.68 g of 3-(4-(1-phenyl-1,3,8-triazaspiro[4.5]-decan-4-one)-2-butynyl)-4-oxothiazolidine oxalate.

Analysis: Calculated for $C_{20}H_{24}N_4O_2S \cdot C_2H_2O_4$: 55.68% C, 5.52% H, 11.81% N; Found: 55.35% C, 5.94% H, 11.81% N.

Example 11 a. 4-Propargyl-1-thia-4-azaspiro[4.4]-nonane-3-one

To 10.0 g of 1-thia-4-azaspiro[4.4]-nonane-3-one in 500 ml anhydrous dimethylformamide was added 4.48 g of potassium hydroxide. The mixture was placed under $N_2$ gas and allowed to stir at room temperature for 30 minutes, after which 7.12 ml of propargyl bromide (80% in toluene) was added. The reaction mixture was allowed to stir overnight (16 hours) at room temperature.

The reaction mixture was poured into an $H_2O/NH_4Cl$ solution and extracted with ethyl acetate. The combined organic layers were washed twice with water and once with brine. The organic layer was dried ($MgSO_4$), filtered and concentrated in vacuo to yield 12 g of a crude oil. The oil was chromatographed using 3:1 hexane:ethyl acetate eluent to give 9.7 g of 4-propargyl-1-thia-4-azaspiro[4.4-nonane-3-one.

b. 4-(4-(1-(2-Methoxyphenyl)piperazino)-2-butynyl)-1-thia-4-azaspiro[4.4]nonane-3-one hydrochloride hydrate To a solution of 4-propargyl-1-thia-4-azaspiro[4.4]nonane-3-one (4.36 g), paraformaldehyde (0.81 g), and 1-(2-methoxyphenyl)piperazine (3.07 g) in 25 ml sieve-dried dioxane was added 0.66 g of cuprous chloride. The reaction was placed under $N_2$ gas and heated to 63° C. After 1½ hours there was no starting amine remaining in the reaction mixture as observed by TLC (100% ethyl acetate, 100% methanol). The reaction mixture was cooled to room temperature, filtered, and concentrated in vacuo. The residue was taken up in ethyl acetate, filtered, and concentrated in vacuo. The residue obtained was chromatographed on silica with ethyl acetate as an eluent and the fractions containing the desired compound concentrated in vacuo. The HCl salt was precipitated from ether yielding 5.24 g of 4-(4-(1-(2-methoxyphenyl)piperazino)-2-butynyl)-1-thia-4-azaspiro[4.4]nonane-3-one hydrochloride hydrate. The product darkened at 70° C. and decomposed at 111°–114° C.

Analysis: Calculated for $C_{22}H_{29}N_3O_2S \cdot HCl \cdot H_2O$: 58.20% C, 7.10% H, 9.26% N; Found: 57.86% C, 6.77% H, 9.12% N.

Example 12

3-(4-[3-(4-piperidyl)-6-chloro-benzisoxazole]-2-butynyl)-4-oxothiazolidine oxalate To a solution of 3-propargyl-4-oxothiazolidine (4.92 g), paraformaldehyde (1.20 g), and 3-(4-piperidyl)-6-chloro-benzisoxazole hydrochloride (5.00 g) in approximately 20 ml sieve-dried dioxane and 9.28 ml triethylamine was added 0.99 g of cuprous chloride. The reaction mixture was heated to 85° C. under $N_2$ gas. After 24 hours, no starting amine remained in the reaction mixture as observed by TLC (silica, 100% methanol, 100% ethyl acetate). The reaction mixture was concentrated in vacuo. The residue was taken up in ethyl acetate and filtered. The filtrate was concentrated down, combined with the filtered solids, and chromatgraphed on silica with ethyl acetate as an eluent. The oxalate salt was precipitated from ethyl acetate and recrystallized from methanol to yield 3.72 g of 3-(4-[3-(4-piperidyl)-6-chloro-benzisoxazole]-butynyl)-4-oxothiazolidine oxalate, m.p. 186°–188° C.

Analysis: Calculated for $C_{19}H_{20}ClN_3O_2S \cdot C_2H_2O_4$: 52.56% C, 4.62% H, 8.76% N; Found: 52.40% C, 4.62% H, 8.78% N.

Example 13

3-(4-1-(4-(4-bromophenoxy)-3-phenyl-piperidyl)-2-butynyl)-4-oxothiazolidine oxalate hydrate To a solution of 3-propargyl-4-oxothiazolidine (3.0 g), paraformaldehyde (0.77 g), and 4-(4-bromophenoxy)-3-phenyl-piperidine (4.68 g) in approximately 25 ml sieve-dried dioxane was added 0.63 g of cuprous chloride. The system was equipped with a reflux condenser, placed under $N_2$ gas, and heated to 90° C. After 3 hours no starting amine remained in the reaction mixture as observed by TLC (silica, 100% methanol). The reaction mixture was cooled to room temperature, filtered, and concentrated in vacuo. The residue was taken up in ethyl acetate, filtered, and concentrated in vacuo to yield an oil. The oil was chromatographed on silica with ethyl acetate eluent and the fractions containing the desired compound were concentrated in vacuo. The oxalate salt was precipitated from ether to yield 4.29 g of 3-(4-1-(4-(4-bromophenoxy)-3-phenyl-piperidyl)-2-butynyl)-4-oxothiazolidine oxalate hydrate. The compound darkened at 72° C. and decomposed at 135° C.

Analysis: Calculated for $C_{24}H_{25}BrN_2O_4S \cdot C_2H_2O_4 \cdot H_2O$: 52.62% C, 4.93% H, 4.72% N; Found: 53.06% C, 4.69% H, 4.88% N.

Example 14

4-(4-(1-(4-Chlorobenzhydryl)piperazino)-2-butynyl)-1-thia-4-azaspiro[4.4]nonane-3-one trisoxalate To a solution of 4-propargyl-1-thia-4-azaspiro[4.4]nonane-3-one (4.98 g), paraformaldehyde (0.92 g), and 1-(4-chlorobenzhydryl)piperazine (3.36 g) in approximately 25 ml sieve-dried dioxane was added 0.76 g of cuprous chloride. The reaction flask was equipped with a reflux condenser, placed under $N_2$ gas, and heated in an oil bath to 81° C. After 2 hours the reaction mixture contained no starting amine as observed by TLC (silica, 100% methanol). The reaction mixture was cooled to room temperature, filtered, and concentrated in vacuo. The residue was chromatographed on silica with ethyl acetate. The oxalate salt was precipitated from ethyl acetate to yield 4.18 g of 4-(4-(1-(4-chlorobenzhydryl)-piperazino)-2-butynyl)-1-thia-4-azaspiro[4.4]nonane-3-one trisoxalate, m.p. 145°-147° C.

Analysis: Calculated for $C_{28}H_{32}ClN_3OS \cdot 3C_2H_2O_4$: 53.44% C, 5.01% H, 5.50% N; Found: 53.26% C, 4.98% H, 5.49% N.

Example 15

2-Methyl-3-(4-(4-(4-bromo)phenoxy)-3-phenyl-piperidyl)-2-butynyl)-4-oxothiazolidine oxalate hemihydrate To a solution of 2-methyl-3-propargyl-4-oxothiazolidine (3.92 g), paraformaldehyde (0.91 g), and 4-(4-bromophenoxy)-3-phenyl-piperidine (5.98 g) in approximately 30 ml sieve-dried dioxane was added 0.75 of cuprous chloride. The reaction flask was equipped with a reflux condenser, placed under $N_2$ gas and heated to 78° C. After 2.5 hours the reaction mixture contained no starting material as observed by TLC (silica, 100% methanol). The reaction mixture was cooled to room temperature, filtered, and concentrated in vacuo. The residue was purified by column chromatography on silica using ethyl acetate as an eluent. The oxalate salt was precipitated from ether to yield 5.97 g of 2-methyl-3-(4-(4-(4-bromo)phenoxy)-3-phenyl-piperidyl)-2-butynyl)-4-oxothiazolidine oxalate hemihydrate, 88° C. (dec).

Analysis: Calculated for $C_{25}H_{27}BrN_2O_2S \cdot C_2H_2O_4 \cdot 0.5H_2O$: 54.18% C, 5.05% H, 4.68% N; Found: 54.23% C, 4.98% H, 4.72% N.

Example 16

2-Methyl-3-(4-1-(2Methoxyphenyl)piperazino-2-butynyl)-4-oxothiazolidine

To a solution of 2-methyl-3-propargyl-4-oxothiazolidine (3.76 g), paraformaldehyde (0.88 g), and 1-(2-methoxyphenyl)piperazine (3.33 g) in approximately 25 ml sieve-dried dioxane was added 0.72 g of cuprous chloride. The reaction flask was equipped with a reflux condenser, placed under $N_2$ gas, and heated in an oil bath to 84° C. After 1 hour the reaction mixture contained no starting material as observed by TLC (silica, 100% methanol). The reaction mixture was cooled to room temperature, filtered, and concentrated in vacuo. The residue was passed through a silica column with ethyl acetate as the eluent. The HCl salt was precipitated from ether. The free base was obtained by placing the salt in 50% KOH solution and extracting 3 times with 300 ml portions of ether. The ether fractions were dried (MgSO$_4$), filtered, and concentrated in vacuo to yield 4.68 g of 2-methyl-3-(4-1-(2-methoxyphenyl)-piperazino-2-butynyl)-4-oxothiazolidine, an oil.

Analysis: Calculated for $C_{19}H_{25}N_3O_2S$: 63.48% C, 7.01% H, 11.69% N; Found: 63.04% C, 7.11% H, 11.49% N.

We claim:

1. A compound of the formula

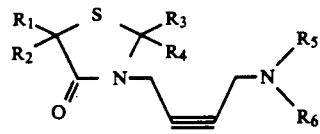

where $R_1$ and $R_2$ are independently hydrogen or loweralkyl or $R_1$ and $R_2$ taken together with the carbon atom to which they are attached form a spiro-fused cycloalkane of 5 to 8 carbons; $R_3$ and $R_4$ are independently hydrogen or loweralkyl or $R_3$ and $R_4$ taken together with the carbon atom to which they are attached form a spiro-fused cycloalkane of 5 to 8 carbons; $R_5$ and $R_6$ taken together with the nitrogen atom to which they are attached are

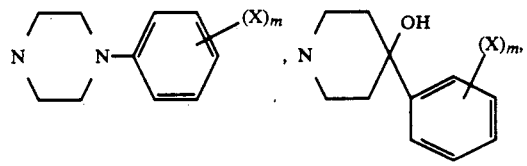

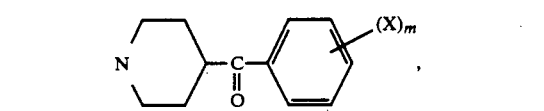

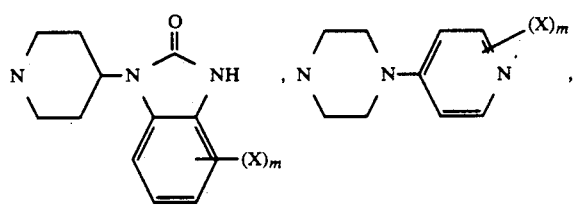

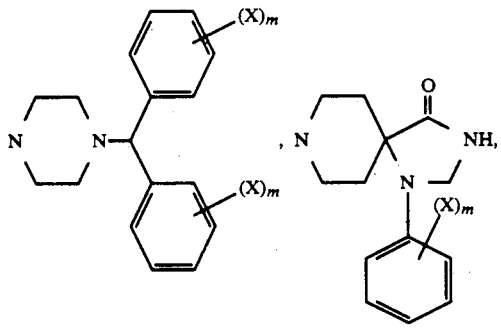

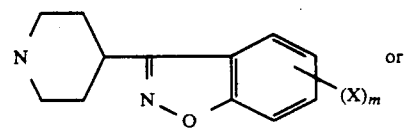

or

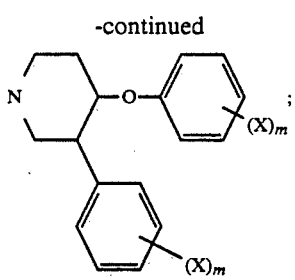

where X in each occurrence is independently hydrogen, halogen, loweralkyl, hydroxy, nitro, amino, cyano, trifluoromethyl or methoxy; and m is 0, 1 or 2; or the pharmaceutically acceptable acid addition salts thereof and where applicable the optical and geometrical isomers and racemic mixtures thereof.

2. The compound according to claim 1 where $R_1$, $R_2$, $R_3$ and $R_4$ are hydrogen.

3. The compound according to claim 1 where $R_1$, $R_2$ and $R_4$ are hydrogen and $R_3$ is alkyl.

4. The compound according to claim 1 where $R_3$ and $R_4$ taken together with the carbon atom to which they are attached form a spiro-fused cycloalkane of 5 to 8 carbons.

5. The compound according to claim 2 which is 3-[4-(1-(2-methoxyphenyl)-piperazino)-2-butynyl]-4-oxothiazolidine or a pharmaceutically acceptable salt thereof.

6. The compound according to claim 2 which is 3-(4-4-(4-fluorobenzoyl)piperidino)-2-butynyl)-4-oxothiazolidine or a pharmaceutically acceptable salt thereof.

7. The compound according to claim 2 which is 3-[4-(4-(1,3-dihydro-2-oxo-2H-benzimidazol-1-yl)piperidino)-2-butynyl]-4-oxothiazolidine or a pharmaceutically acceptable salt thereof.

8. The compound according to claim 2 which is 3-(4-(1-(4-fluorophenyl)piperazino)-2-butynyl-4-oxothiazolidine or a pharmaceutically acceptable salt thereof.

9. The compound according to claim 2 which is 3-(4-(4-pyridyl)piperazino)-2-butynyl)-4-oxothiazolidine or a pharmaceutically acceptable salt thereof.

10. The compound according to claim 2 which is 3-(4-(1-(4-chlorobenzhydryl)-piperazino)-2-butynyl)-4-oxothiazolidine or a pharmaceutically acceptable salt thereof.

11. The compound according to claim 2 which is 3-(4-(1-phenyl-1,3,8-triazaspiro[4.5]-decan-4-one)-2-butynyl)-4-oxothiazolidine or a pharmaceutically acceptable salt thereof.

12. The compound according to claim 2 which is 3-(4-[3-(4-piperidyl)-6-chlorobenzisoxazole]-2-butynyl)-4-oxothiazolidine or a pharmaceutically acceptable salt thereof.

13. The compound according to claim 2 which is 3-(4-1-(4-(4-bromophenoxy)-3-phenyl-piperidyl)-2-butynyl)-4-oxothiazolidine or a pharmaceutically acceptable salt thereof.

14. The compound according to claim 3 which is 2-methyl-3-(4-(4-hydroxy-4-phenylpiperidino)-2-butynyl)-4-oxothiazolidine or a pharmaceutically acceptable salt thereof.

15. The compound according to claim 3 which is 2-methyl-3-(4-(4-(4-bromo)phenoxy)-3-phenyl-piperidyl)-2-butynyl)-4-oxothiazolidine or a pharmaceutically acceptable salt thereof.

16. The compound according to claim 3 which is 2-methyl-3-(4-1-(2-methoxyphenyl)piperazino-2-butynyl)-4-oxothiazolidine or a pharmaceutically acceptable salt thereof.

17. The compound according to claim 4 which is 4-(4-(1-(2-methoxyphenyl)piperazino)-2-butynyl)-1-thia-3-azaspiro[4.4]nonane-3-one or a pharmaceutically acceptable salt thereof.

18. The compound according to claim 4 which is 4-(4-(1-(4-chlorobenzhydryl)-piperazino)-2-butynyl)-1-thia-4-azaspiro[4.4]nonane-3-one or a pharmaceutically acceptable salt thereof.

19. An analgesic composition comprising an effective pain alleviating amount of a compound as defined in claim 1 and a suitable carrier therefor.

20. An antihypertensive composition comprising an effective blood pressure lowering amount of a compound as defined in claim 1 and an inert, blood pressure reducing adjuvant.

21. A method of treating a patient in need of relief from pain which comprises administration of an effective pain alleviating amount of a compound as defined in claim 1.

22. A method of treating a patient in need of relief from hypertension which comprises administration of an effective blood pressure reducing amount of a compound as defined in claim 1.

* * * * *